United States Patent [19]
Portnoff

[11] 4,087,538
[45] May 2, 1978

[54] OPHTHALMIC SUSPENSIONS

[75] Inventor: Joel B. Portnoff, Philadelphia, Pa.

[73] Assignee: Merck & Co., Inc., Rahway, N.J.

[21] Appl. No.: 721,922

[22] Filed: Sep. 9, 1976

[51] Int. Cl.² .............................................. A61K 31/40
[52] U.S. Cl. .................................................... 424/274
[58] Field of Search ........................................ 424/274

[56] References Cited
PUBLICATIONS

Chem. Abst–67–31281e (1967).

MSD–Price List No. 69: "Pharmaceuticals/Biologicals" Apr. 15, 1976.

*Primary Examiner*—Stanley J. Friedman
*Attorney, Agent, or Firm*—Raymond M. Speer; Mario A. Monaco

[57] ABSTRACT

Improved anti-inflammatory suspensions for ophthalmic applications, comprising 1-(p-chlorobenzoyl)-2-methyl-5-methoxy-3-indolyl acetic acid as active ingredient.

2 Claims, No Drawings

OPHTHALMIC SUSPENSIONS

BACKGROUND OF THE INVENTION

Many useful opthalmic compounds are solids. Those solids which are soluble in ophthalmic carriers or vehicles present little or no difficulty when preparing a formulation for ophthalmic use. However, those solids which are insoluble in opthalmic carriers must be formulated as suspensions in order to obtain a proper delivery system. Moreover, forms of useful opthalmic compounds which are insoluble in ophthalmic carriers are often found desirable in order to prolong the particular therapeutic action of the compound. Consequently, providing acceptable suspensions of useful ophthalmic compounds is a goal of pharmaceutical formulation.

An acceptable ophthalmic suspension possesses certain essential characteristics, among which are: that the suspended material should not settle too rapidly from the carrier to be available in the required concentration in the carrier for effective administration to the eye of the patient; that the particles of suspended material which do finally settle to the bottom of the vessel holding the suspension must not form an intractable hard cake but should be readily redispersed into a uniform suspension when the vessel is shaken; and that the total suspension must not be too viscous for efficient administration to the eye of the patient, but should pour freely.

Suspensions are prepared by use of either, vehicles structured to maintain discrete particles more or less permanently in suspension, without agglomeration or flocculation, or by the application of known principles of formulation chemistry of produce vehicles which permit flocs to form and settle, but in which they are easily resuspended with slight agitation and remain uniformly dispersed or suspended during the period required for therapeutic administration. In this latter approach, flocculating agents are used in preparing the vehicle or carrier. However, depending upon the type of medicinal product employed, particular ratios of medicament, carrier and flocculating agent must be employed. These critical ratios cannot be determined beforehand and with some medicaments are extremely difficult to obtain at all.

There is a known anti-inflammatory agent useful in therapeutic treatment of inflammatory diseases of the eye; namely 1-(p-chlorobenzoyl)-2-methyl-5-methoxy-3-indolyl acetic acid, which is insoluble in conventional ophthalmic carriers and consequently must be employed in the form of suspensions. However, use of this medicament has been impeded by the fact that it does not readily form acceptable suspensions in vehicles containing flocculating agents in the proportions normally employed in ophthalmic suspensions.

SUMMARY OF THE INVENTION

It has been found that, in accordance with the present invention, acceptable ophthalmic suspensions for treating inflammation in the mammalian, human and animal, eye, using 1-(p-chlorobenzoyl)-2-methyl-5-methoxy-3-indolyl acetic acid, can be prepared by employing certain flocculating agents and deflocculating or suspending agents together, and by employing certain critical ratios of the various proportional amounts of medicament, vehicle, flocculating agent and deflocculating agent in the total suspension. Thus, the present invention relates to a composition of matter in the form of an improved ophthalmic suspension comprising from 1 to 15 mg./ml. of total suspension of the medicament, deflocculating agent as hereinafter defined, and flocculating agent as hereinafter defined, provided that the ratio of flocculating agent to deflocculating agent is from 7:1 to 30:1, especially 10:1 to 15:1, respectively, and the ratio of medicament to deflocculating agent is from 300:1 to 1:2, especially 60:1 to 1:1, respectively. In its preferred aspect, however, the ophthalmic suspension composition of the present invention will contain from 1 to 15 mg./ml. and especially 2.5 to 10 mg./ml. of total suspension of medicament; 0.05 to 1.7 mg./ml. and especially 0.15 to 1.5 mg./ml. of total suspension of deflocculating agent; and 3 to 17 mg./ml. and especially 4 to 15 mg./ml. of total suspension of flocculating agent. The ophthalmic suspension compositions of the present invention also contain certain excipients whose presence is desirable in preparing an acceptable ophthalmic suspension. The nature and proportional amounts of these excipients will be discussed in detail hereinafter.

The flocculating agents employed in preparing the ophthalmic suspension compositions of the present invention, while not regarded conventionally as flocculating agents, do, in fact, flocculate the medicament from the ophthalmic suspensions of the present invention. Flocculation is the aggregation of essentially monodispersed particles in a liquid into a light, fluffy agglomerate (floc) which separates from the liquid. The floc is formed and maintained primarily by weak Van der Waals forces. Flocculation is readily mediated by flocculating agents, which may be generally characterized by type as electrolytes, surfactants and polymers. While these types of flocculating agents produce flocculation by different mechanisms, the overall result is the same. The flocculating agents employed in the present invention are alkanols of 1 to 4 carbon atoms, and aromatic alcohols selected from the group consisting of benzyl alcohol, $\beta$-phenylethyl alcohol and cinnamyl alcohol, and mixtures of the above. Mixtures of varying proportions are suitable, and, for example, a mixture of benzyl alcohol and $\beta$-phenylethyl alcohol in a ratio of approximately 1:1 by weight has been found to give excellent results. As indicated previously, the flocculating agent will be employed in the ophthalmic suspension in amounts such that the ratio of flocculating agent to deflocculating agent is from 7:1 to 30:1, especially 10:1 to 15:1, respectively.

The deflocculating or suspending agents employed in the ophthalmic suspension compositions of the present invention are products derived from the condensation of polymers of ethylene oxide containing from 10 to 50 oxyethylene repeating units, and esters of fat acids of 10 to 18 carbon atoms. Especially suitable are such condensation products from fat acid esters of sorbitol, particularly the lauric, stearic and oleic acid esters of sorbitol. The fat acid esters may be employed as mixtures from naturally occurring oils, which are esters of fat acids and glycerol. Thus, the deflocculating agent may be polyoxyethylene vegetable oil, available as Emulphor EL-719 from GAF Corporation. Naturally occurring fat acid mixtures may be employed to produce esters of sorbitol for condensation with polyoxyethylene. Thus, the deflocculating agent may be polyoxyethylene sorbitol lanolin, polyoxyethylene sorbitol tallow esters, and polyoxyethylene sorbitol tall oil, available, respectively, as Atlas G-1441, Atlas G-3284, and Atlox 1256 from Atlas Chemical Industries. Particularly preferred are esters of sorbitol and specific fat acids, especially lauric, stearic and oleic acids. Thus, the deflocculating agent may be polyoxyethylene sorbitan monolaurate, polyoxyethylene sorbitan monostearate, or polyoxyethylene sorbitan monooleate, available, respectively, as Atlas G-7596J, Tween 80 from Atlas Chemical Industries. The last named product, Tween 80, which contains 20 oxyethylene units, has been found to be especially suitable. As indicated previously, the deflocculating agent will be employed in the ophthalmic suspension in amounts such that the ratio of medicament to deflocculating agent is from 300:1 to 1:2, especially 60:1 to 1:1, respectively.

By use of the particular flocculating and deflocculating agents described above, and in the critical range of proportionate amount ratios of the present invention, it is possible to obtain acceptable ophthalmic suspension compositions for 1-(p-chlorobenzoyl)-2-methyl-5-methoxy-3-indolyl acetic acid, which have the highly desirable properties of having the suspended material uniformly dispersed therein during the period of administration to the eye of the patient, while at the same time facilitating easy redispersion of that material after its flocculation and separation in the ophthalmic suspension composition. The problem thus avoided is that of caking, whereby the layer of material formed by flocculation and separation experiences a fusing together of the separate floc aggregates into larger masses until a consolidated, compact and near-monolithic formation is established. The result, of course, is an intractable hard cake which is highly resistant to redispersion.

In addition to the medicament, flocculating and deflocculating agents and water, conventional excipients and other materials are advantageously employed in preparing the ophthalmic suspension compositions of the present invention in accordance with good pharmaceutical practice. For example, the ophthalmic suspensions are sterile and preferably contain a bacteriological preservative to maintain sterility during use. Quarternary ammonium bacteriostats such as benzalkonium chloride may be used as well as phenyl mercuric acetate, phenyl mercuric nitrate, thimerosal, benzyl alcohol, or β-phenylethyl alcohol. These bacteriostats may suitably be used in a range of from 0.01 to 3.0. mg./ml. and preferably 0.1 to 0.2 mg./ml. of total suspension. An anti-oxidant may also be used to prevent oxidation of the medicament. Suitable anti-oxidants include sodium bisulfate, N-acetyl cysteine salts, sodium ascorbate, sodium meta bisulfite, sodium acetone bisulfite and other acceptable anti-oxidants known to the pharmaceutical art. These anti-oxidants may suitably be used in a range of 0.1 to 10.0 mg./ml. and preferably 0.2 to 3.5 mg./ml. In conjunction with the anti-oxidants, chelating agents such as disodium edetate may also be employed.

Viscosity inducing agents helpful in suspension characteristics of the composition, including cellulose derivatives such as hydroxymethyl cellulose, hydroxypropyl cellulose and methyl cellulose, may also be used in the formulation. For this purpose, one may use from 5.0 to 10.0 mg./ml. and preferably from 1.5 to 3.5 mg./ml. of such agents. Lecithin may also be used to provide helpful suspension characteristics for the ophthalmic suspension composition, being employed for this purpose in amounts of from 0.05 to 1.0 mg./ml. of total suspension, and preferably from 0.1 to 0.4 mg./ml. A humectant is also sometimes used to help retain the water of the formulation in the eye. High molecular weight sugars are suitably used for this purpose such as sorbitol and dextrose in a concentration of from 0.1 to 10.0 mg./ml. and especially 0.5 to 2.0 mg./ml. Finally, since the formulation is autoclaved to obtain initial sterility an autoclaving aid such as sodium chloride is normally added to the formulation. The ophthalmic suspension compositions of the present invention are prepared by methods well known in the pharmaceutical art. For example, (1) there is first prepared a supersaturated NaCl aqueous solution such that the volume of water does not exceed 2 ½ times the amount of NaCl, and excess NaCl remains undissolved. (2) The medicament is then dispersed in the saline solution of (1) until a wet paste is formed. (3) The paste is sterilized by autoclaving at 121° C. under 15 p.s.i.g. pressure. (4) The viscosity inducing agent which is employed is then dispersed in water, clarified, and sterilized by autoclaving. (5) The other components of the total suspension composition are then added to water to form a solution. (6) The medicament paste from step (3) is then added aseptically to the viscosity inducing agent dispersion of step (4), and mixed. (7) The remaining suspension ingredients, prepared in step (5), are added aseptically to the mixture from step (6) by way of sterilizing membrane. (8) Sufficient water is added to the suspension from step (7) to give the total desired volume. (9) The suspension is then aseptically homogenized at 1500-2200 p.s.i.g., subdivided and distributed to suitable sterile containers.

DESCRIPTION OF SPECIFIC EMBODIMENTS

The following examples illustrate preparation of the improved ophthalmic suspension compositions of the present invention, and the improved characteristics thereof.

EXAMPLES 1-4

The following materials were admixed in a 1250 ml. bottle: 20.6 g. of 1-(p-chlorobenzoyl)-2-methyl-5-methoxy-3-indolyl acetic acid, which was a sufficient amount of medicament to result in a concentration of 10 mg. per ml. in the final samples, allowing for previously established 3.0% overage; 0.4 g. sodium bisulfite, 12 g. NaCl, and 28 ml. water (at 180° F.). The mixture (I) was autoclaved for 30 minutes at 121° C. under 15 p.s.i.g. Separately, 3 g. of hydroxyethylcellulose in 720 ml. of water (II) and 0.4 g. of lecithin in 80 ml. of water (III) were autoclaved for 30 minutes at 121° C. Then, III was admixed with I for 2 hours, and the resultant mixture was poured into II. Another mixture (IV) was prepared from 20 g. of sorbitol, 2.36 ml. of benzalkonium chloride, 10 g. of disodium edetate, and water to give a final solution volume of 900 ml. Then, IV was added to the mixture of I, II, and III in sufficient quantity to give 1.8 l. overall. The 1.8 l. mixture of I, II, III, and IV was then taken and homogenized using an homogenizer at 2000 p.s.i.g. Stock solutions were then prepared for polyoxyethylene (20) sorbitan monooleate by dissolving 3 g. of the material in 100 ml. of water, and of benzyl alcohol/β-phenylethyl alcohol by admixing 50 ml. of each alcohol. Varying quantities of the two stock solutions were then added to four 90 ml. aliquots of the homogenized mixture of I, II, III, and IV prepared as described above, together with sufficient water to give a total of 100 ml. for each of four different samples. The quantities of flocculating agent and deflocculating agent employed and the results obtained are noted in the following table of values.

| Example No. | Polyoxyethylene (20) sorbitan monooleate mg./ml. | Benzyl alcohol/ β-phenyl-ethyl alcohol (mg./ml.) | Original Suspension Character (at 4 days) | | | Suspension Character After 7 Months | |
|---|---|---|---|---|---|---|---|
| | | | Degree of Flocculation | Number of Gentle Inversions required for resuspension | Sediment Volume | Number of Gentle Inversions required for resuspension | Sediment Volume |
| 1 | 0.375 | 2.5/2.5 | good | 2 | 8% | 2 | 6.5% |
| 2 | 0.188 | 2.5/2.5 | good | 2 | 8% | 2 | 7.5% |
| 3 | 1.5 | 5.0/5.0 | good | 2 | 7% | 2 | 6.5% |
| 4 | 1.5 | 7.5/7.5 | good | 2 | 5% | 3 | 4% |

EXAMPLES 5-7

For purposes of comparison, the procedures of Examples 1-4 were repeated, but using more extreme amounts and ratios of the stock solution materials. The results obtained are noted in the following table of values.

| Example No. | Polyoxyethylene (20) sorbitan monooleate mg./ml. | Benzyl alcohol/ β-phenyl-alcohol (mg./ml.) | Original Suspension Character (at 4 days) | | | Suspension Character After 7 Months | |
|---|---|---|---|---|---|---|---|
| | | | Degree of Flocculation | Number of Gentle Inversions required for resuspension | Sediment Volume | Number of Gentle Inversions required for resuspension | Sediment Volume |
| 5 | 1.5 | 2.5/2.5 | fair/poor | 7 | <2% | >10 (lumps) | <2% |
| 6 | 1.5 | 1.25/1.25 | poor | 7 | 3% | 10 (lumps) | <2% |
| 7 | 1.5 | 10.0/10.0 | too large | 2 | 5% | 3 (gritty and large) | 5% |

EXAMPLE 8

The following procedures were followed in preparing a 5.1 batch of an acceptable ophthalmic suspension in accordance with the present invention, of 1-(p-chlorobenzoyl)-2-methyl-5-methoxy-3-indolyl acetic acid. The therapeutic dosage concentration of the total final batch was 10 mg./ml. of medicament in the total suspension. However, dosage concentrations of the medicament of 5 mg./ml. and 2.5 mg./ml. may also be prepared following the same procedures, varying only the initial amount of medicament employed, proportionally to yield the resultant smaller dosage concentrations. A first mixture (I) was prepared by mixing in a 1250 ml. bottle: 1 g. sodium bisulfite, 30 g. NaCl, 70 ml. water, and 51.5 g. 1-(p-chlorobenzoyl)-2-methyl-5-methoxy-3-indolyl acetic acid. A second mixture (II) was prepared by dissolving 1 g. of lecithin in 225 ml. water. A third (III) mixture was prepared by admixing 7.5 g. of hydroxyethylcellulose in 1.5 l. water, and bringing the total volume to 2.0 l. after the initial mixture clarified. Finally, a fourth mixture (IV) of the remaining suspension ingredients was prepared by admixing 1.88 g. polyoxyethylene (20) sorbitan monooleate, 1.0 g. benzalkonium chloride, 12.5 g. benzyl alcohol, 12.5 g. β-phenylethyl alcohol, 50.0 g. of sorbitol as aqueous solution, and 2.5 g. disodium edetate. All four mixtures were sterilized by autoclaving for 30 minutes at 121° C. under 15 p.s.i.g. Then, mixture II was added to I, and this mixture, in turn, was added to mixture III. Finally, mixture IV was added aseptically to the mixture of I, II and III by way of sterilizing membrane, and the total suspension volume was brought to 5.1 with sterile water. The suspension was homogenized at 1500 p.s.i.g. and filled into containers.

What we claim is:

1. An ophthalmic suspension composition comprising 10 mg./ml. of total suspension of a medicament composition comprising 1-(p-chlorobenzoyl)-2-methyl-5-methoxy-3-indolyl acetic acid; 0.375 to 1.5 mg./ml. of total suspension of a deflocculating agent comprising polyoxyethylene (20) sorbitan monooleate; 5.0 to 15.0 mg./ml. of total suspension of a flocculating agent comprising benzyl alcohol and β-phenylethyl alcohol in a 1:1 weight ratio; and water.

2. The composition of claim 1 wherein there is present a viscosity inducing agent, a preservative, an antioxidant, a chelating agent, a humectant and an autoclaving aid.

* * * * *

UNITED STATES PATENT OFFICE
CERTIFICATE OF CORRECTION

Patent No. 4,087,538    Dated May 2, 1978

Inventor(s) Joel B. Portnoff

It is certified that error appears in the above-identified patent and that said Letters Patent are hereby corrected as shown below:

The term of this patent subsequent to June 6, 1995 has been disclaimed.

Signed and Sealed this

Fourth Day of July 1978

[SEAL]

Attest:

RUTH C. MASON
Attesting Officer

DONALD W. BANNER
Commissioner of Patents and Trademarks